United States Patent
Sun et al.

(10) Patent No.: US 12,319,636 B2
(45) Date of Patent: Jun. 3, 2025

(54) 2-CHLORO-3,3,3-TRIFLUOROPROPENE (1233XF) COMPOSITIONS AND METHODS FOR MAKING AND USING THE COMPOSITIONS

(71) Applicant: THE CHEMOURS COMPANY FC, LLC, Wilmington, DE (US)

(72) Inventors: Xuehui Sun, Kennett Square, PA (US); Karl Robert Krause, Kennett Square, PA (US); Andrew Jackson, Newark, DE (US)

(73) Assignee: THE CHEMOURS COMPANY FC, LLC, Wilmington, DE (US)

( * ) Notice: Subject to any disclaimer, the term of this patent is extended or adjusted under 35 U.S.C. 154(b) by 732 days.

(21) Appl. No.: 17/614,314

(22) PCT Filed: Jun. 3, 2020

(86) PCT No.: PCT/US2020/035817
§ 371 (c)(1),
(2) Date: Nov. 24, 2021

(87) PCT Pub. No.: WO2020/247423
PCT Pub. Date: Dec. 10, 2020

(65) Prior Publication Data
US 2023/0183155 A1 Jun. 15, 2023

Related U.S. Application Data

(60) Provisional application No. 62/857,082, filed on Jun. 4, 2019.

(51) Int. Cl.
*C07C 21/18* (2006.01)
*C07C 19/10* (2006.01)

(52) U.S. Cl.
CPC ............. *C07C 21/18* (2013.01); *C07C 19/10* (2013.01)

(58) Field of Classification Search
CPC ....... C07C 21/18; C07C 19/10; C07C 17/087; C07C 17/206; C07C 17/205
See application file for complete search history.

(56) References Cited

U.S. PATENT DOCUMENTS

| 4,978,649 | A | 12/1990 | Surovikin et al. |
| 5,136,113 | A | 8/1992 | Rao |
| 5,155,082 | A | 10/1992 | Tung et al. |
| 2009/0182179 | A1 | 7/2009 | Merkel et al. |
| 2011/0270000 | A1 | 11/2011 | Bektesevic et al. |
| 2012/0078020 | A1 | 3/2012 | Elsheikh et al. |
| 2012/0215035 | A1 | 8/2012 | Nappa |
| 2012/0215935 | A1 | 8/2012 | Woods |
| 2012/0302803 | A1* | 11/2012 | Yamashita ............... C07C 17/25 570/156 |
| 2015/0057472 | A1 | 2/2015 | Bektesevic et al. |
| 2015/0259267 | A1 | 9/2015 | Sun et al. |
| 2016/0023972 | A1 | 1/2016 | Nair et al. |
| 2016/0355453 | A1 | 12/2016 | Ohkubo et al. |
| 2017/0253545 | A1* | 9/2017 | Bektesevic ............. C07C 17/42 |
| 2017/0313639 | A1* | 11/2017 | Wang .................... C07C 17/386 |
| 2019/0031584 | A1* | 1/2019 | Deur-Bert ............. C07C 17/206 |
| 2019/0367434 | A1* | 12/2019 | Sharratt .................. C07C 17/25 |
| 2021/0317256 | A1* | 10/2021 | Shtern ..................... C08J 9/146 |

FOREIGN PATENT DOCUMENTS

| CN | 103483142 A | 1/2014 |
| CN | 105218297 B | 8/2017 |
| EP | 2080748 A2 | 7/2009 |
| JP | 2011038054 A | 2/2011 |
| JP | 2017014160 A | 1/2017 |
| WO | 2009137658 A2 | 11/2009 |
| WO | 2010141527 A1 | 12/2010 |
| WO | 2011056441 A2 | 5/2011 |
| WO | 2011102538 A2 | 8/2011 |
| WO | 2011146820 A2 | 11/2011 |
| WO | 2014025065 A1 | 2/2014 |
| WO | 2017044724 A1 | 3/2017 |
| WO | 2017129878 A1 | 8/2017 |
| WO | 2019030527 A1 | 2/2019 |
| WO | 2019203318 A1 | 10/2019 |

OTHER PUBLICATIONS

Dai, et al., Construction of β-Trifluoromethyl Enol Ether via Base-Promoted C—O Coupling and Rearrangement of Hydrogen Atom, Journal of Organic Chemistry, 2017, pp. 4721-4728, vol. 82.
Haszeldine, R. N., Reactions of fluorocarbon radicals. Part V. Alternative syntheses for trifluoromethylacetylene (3 : 3 : 3-trifluoropropyne), and the influence of polyfluoro-groups on adjacent hydrogen and halogen atoms, Journal of the Chemical Society, Jan. 1, 1951, pp. 2495-2506.
International Search Report and Written Opinion for PCT/US2020/035817 mailed Sep. 17, 2020.

* cited by examiner

Primary Examiner — Jafar F Parsa

(57) ABSTRACT

A composition including 2-chloro-3,3,3-trifluoropropene (1233xf), one or more of 2,3-dichloro-1,1,1-trifluoropropane (243db), 1,2-dichloro-3,3,3-trifluoropropene (1223xd), 2,3-dichloro-3,3-difluoropropene (1232xf), 2,2,3-trichloro-1,1,1-trifluoro-propane (233ab), 2,3,3-trichloro-1,1,1-trifluoropropane (233da), 3,3,3-trifluoropropyne, 1-chloro-3,3,3-trifluoropropyne, 3,3,3-trifluoro-1-propene (1243zf), 1-chloro-3,3,3-trifluoro-1-propene (1233zd), 1-chloro-2,3,3,3-tetrafluoro-1-propene (1224yd), or 2-bromo-3,3,3-trifluoropropene and optionally 1233xf oligomers are disclosed.

23 Claims, No Drawings

2-CHLORO-3,3,3-TRIFLUOROPROPENE (1233XF) COMPOSITIONS AND METHODS FOR MAKING AND USING THE COMPOSITIONS

This application claims the benefit of U.S. Application No. 62/857,082, filed on Jun. 4, 2019. The disclosure of Application No. 62/857,082 is incorporated by reference.

FIELD

The present invention is directed to 2-chloro-3,3,3-trifluoropropene (1233xf) compositions. More particularly, the present invention is directed to 2-chloro-3,3,3-trifluoropropene (1233xf) compositions as heat transfer fluids, refrigerants, and reactive intermediates.

BACKGROUND

Hydrofluorocarbons (HFCs), such as hydrofluoro-olefins, have been disclosed as effective refrigerants, fire extinguishants, heat transfer media, propellants, foaming agents, blowing agents, gaseous dielectrics, sterilant carriers, polymerization media, particulate removal fluids, carrier fluids, buffing abrasive agents, displacement drying agents and power cycle working fluids. Hydrofluoro-olefins have replaced chlorofluorocarbons and hydrochlorofluorocarbons, which can potentially damage the Earth's ozone layer. Many hydrofluorocarbons exhibit a high global warming potential (GWP). However, hydrofluoro-olefins have a short atmospheric lifespan, due to their reactive olefin bond, and thus do not extensively contribute to global warming.

SUMMARY

In one embodiment, disclosed herein are compositions useful as refrigerants and heat transfer fluids. Compositions disclosed herein can be used as an intermediate to produce 1234yf which can be used as low GWP refrigerant, heat transfer media, blowing agent, or solvent. Compositions disclosed herein can also be used as an intermediate to produce 244bb which in turn is a precursor to 1234yf which can be used as low GWP refrigerant, heat transfer media, blowing agent, or solvent. Compositions disclosed hereby can further be used as a source of trifluoromethyl group (—CF3) to produce a wide range of organic compounds, such as pharmaceuticals, agricultural chemicals, and functional materials (e.g., Journal of Organic Chemistry, 82(9), 4721-4728; 2017); a precursor for making 1223xd (e.g., JP2017014160) and a precursor for making 1336mzz (e.g., U.S. Pat. Appl. Publ., 20160023972 and CN105218297). The disclosure of the foregoing publications is hereby incorporated by reference.

The compositions disclosed herein comprise: a) 2-chloro-3,3,3-trifluoropropene (1233xf); and b) at least one of 2,3-dichloro-1,1,1-trifluoropropane (243db), 1,2-dichloro-3,3,3-trifluoropropene (1223xd), 2,3-dichloro-3,3-difluoropropene (1232xf), 2,2,3-trichloro-1,1,1-trifluoropropane (233ab), 2,3,3-trichloro-1,1,1-trifluoro-propane (233da), 3,3,3-trifluoropropyne, 1-chloro-3,3,3-trifluoropropyne, 3,3,3-trifluoro-1-propene (1243zf), 1-chloro-3,3,3-trifluoro-1-propene (1233zd), 1-chloro-2,3,3,3-tetrafluoro-1-propene (1224yd), or 2-bromo-3,3,3-trifluoropropene.

According to any of the foregoing embodiments, also disclosed herein are compositions wherein b) includes 2,3-dichloro-1,1,1-trifluoropropane (243db).

According to any of the foregoing embodiments, also disclosed herein are compositions wherein b) includes 1-chloro-3,3,3-trifluoropropyne.

According to any of the foregoing embodiments, also disclosed herein are compositions wherein b) includes 2-bromo-3,3,3-trifluoropropene.

According to any of the foregoing embodiments, also disclosed herein are compositions wherein b) includes 1,2-dichloro-3,3,3-trifluoropropene (1223xd).

In another embodiment, disclosed herein are 2-chloro-3,3,3-trifluoropropene (1233xf) composition produced by the steps of: contacting 2,3-dichloro-1,1,1-trifluoropropane (243db), in the liquid phase, with a base to effect dehydrochlorination to form 2-chloro-3,3,3-trifluoropropene (1233xf).

According to any of the foregoing embodiments, also disclosed herein are compositions wherein the 2,3-dichloro-1,1,1-trifluoropropane (243db) is contacted with the base in the presence of a catalyst.

According to any of the foregoing embodiments, also disclosed herein are compositions wherein the 2,3-dichloro-1,1,1-trifluoropropane (243db) is contacted with the base in the absence of a catalyst.

According to any of the foregoing embodiments, also disclosed herein are compositions wherein the base includes at least one of sodium carbonate, potassium carbonate, sodium hydroxide, potassium hydroxide, potassium tert-butoxide, calcium oxides, or calcium hydroxide.

According to any of the foregoing embodiments, also disclosed herein are compositions wherein the composition includes 2-chloro-3,3,3-trifluoropropene (1233xf) and at least one of 1-chloro-3,3,3-trifluoro-1-propene (1233zd), 2,3-dichloro-1,1,1-trifluoropropane (243db), 1,2-dichloro-3,3,3-trifluoropropene (1223xd), 2,3-dichloro-3,3-difluoropropene (1232xf), 2,2,3-trichloro-1,1,1-trifluoro-propane (233ab), 2,3,3-trichloro-1,1,1-trifluoro-propane (233da), 3,3,3-trifluoropropyne, 1-chloro-3,3,3-trifluoropropyne, or 2-bromo-3,3,3-trifluoropropene.

In yet another embodiment, disclosed herein are 2-chloro-3,3,3-trifluoropropene (1233xf) compositions produced by the steps of: contacting 2,3-dichloro-1,1,1-trifluoropropane (243db), in the vapor phase, with a dehydrochlorination catalyst at a temperature and pressure sufficient to effect dehydrochlorination to form 2-chloro-3,3,3-trifluoropropene (1233xf).

According to any of the foregoing embodiments, also disclosed herein are compositions wherein the dehydrochlorination catalyst comprises activated carbon, alumina, chromium oxide, oxides of transition metals, or metal halides.

According to any of the foregoing embodiments, also disclosed herein are compositions wherein the composition includes 2-chloro-3,3,3-trifluoropropene (1233xf) and at least one of 2,3-dichloro-1,1,1-trifluoropropane (243db), 1,2-dichloro-3,3,3-trifluoropropene (1223xd), 2,3-dichloro-3,3-difluoropropene (1232xf), 2,2,3-trichloro-1,1,1-trifluoro-propane (233ab), 2,3,3-trichloro-1,1,1-trifluoro-propane (233da), 3,3,3-trifluoropropyne, 1-chloro-3,3,3-trifluoropropyne, or 2-bromo-3,3,3-trifluoropropene.

In yet another embodiment, disclosed herein are 2-chloro-3,3,3-trifluoropropene (1233xf) compositions produced by the steps of: contacting a compound selected from the group consisting of 1,1,1,2,3-pentachloropropane (HCC-240db), 2,3,3,3-tetrachloropropene (1230xf), 1,1,2,3-tetrachloropropene (HCC-1230xa), 2,3-dichloro-1,1,1-trifluoropropane (243db) and combinations thereof, in the vapor phase, with a fluorination catalyst in the presence of hydrogen fluoride at a temperature and pressure sufficient to effect formation of 2-chloro-3,3,3-trifluoropropene (1233xf).

According to any of the foregoing embodiments, also disclosed herein are compositions wherein the fluorination catalyst comprises chromium, aluminum, cobalt, manganese, nickel or iron oxides, hydroxides, halides, oxyhalides, or inorganic salts thereof.

In yet another embodiment, disclosed herein are 2,3,3,3-tetrafluoropropene (1234yf) compositions produced by the steps of: contacting 2-chloro-3,3,3-trifluoropropene (1233xf) with hydrogen fluoride in the presence of a fluorination catalyst at a temperature sufficient to effect formation of 2-chloro-1,1,1,2-tetrafluoropropene (244bb); and thermally dehydrochlorinating the 2-chloro-2,3,3,3-tetrafluoropropane (244bb) to 1234yf, or contacting the 2-chloro-2,3,3,3-tetrafluoropropane (244bb) with a vapor phase dehydrochlorination catalyst to effect dehydrochlorination to form 2,3,3,3-tetrafluoropropene (1234yf), or contacting the 2-chloro-2,3,3,3-tetrafluoropropane (244bb) with a base at a temperature sufficient to effect dehydrochlorination to form 2,3,3,3-tetrafluoropropene (1234yf).

According to any of the foregoing embodiments, also disclosed herein are compositions wherein the 2-chloro-3,3,3-trifluoropropene (1233xf) is contacted with the hydrogen fluoride in the vapor phase.

According to any of the foregoing embodiments, also disclosed herein are compositions wherein the 2-chloro-3,3,3-trifluoropropene (1233xf) is contacted with the hydrogen fluoride in the liquid phase.

According to any of the foregoing embodiments, also disclosed herein are compositions wherein the 2-chloro-1,1,2-tetrafluoropropene (244bb) is converted to 1234yf in the vapor phase in the presence of a catalyst.

According to any of the foregoing embodiments, also disclosed herein are compositions wherein the 2-chloro-1,1,2-tetrafluoropropene (244bb) is converted to 1234yf in the vapor phase in the absence of a catalyst.

According to any of the foregoing embodiments, also disclosed herein are compositions wherein the 2-chloro-1,1,2-tetrafluoropropene (244bb) is contacted with the base in the liquid phase.

In yet another embodiment, disclosed herein are 2,3,3,3-tetrafluoropropene (1234yf) compositions produced by the steps of: contacting any of the foregoing 2-chloro-3,3,3-trifluoropropene (1233xf) containing compositions in the vapor phase, with hydrogen fluoride in the presence of a fluorination catalyst at a temperature sufficient to effect formation of 2-chloro-1,1,1,2-tetrafluoropropene (244bb); and thermally dehydrochlorinating the 2-chloro-2,3,3,3-tetrafluoropropane (244bb) to 1234yf, or contacting the 2-chloro-2,3,3,3-tetrafluoropropane (244bb) with a vapor phase dehydrochlorination catalyst to effect dehydrochlorination to form 2,3,3,3-tetrafluoropropene (1234yf), or contacting the 2-chloro-2,3,3,3-tetrafluoropropane (244bb) with a base at a temperature sufficient to effect dehydrochlorination to form 2,3,3,3-tetrafluoropropene (1234yf).

According to any of the foregoing embodiments, also disclosed herein are compositions wherein the 2-chloro-2,3,3,3-tetrafluoropropane (244bb) is contacted with the base in the liquid phase.

According to any of the foregoing embodiments, also disclosed herein are compositions wherein the 2-chloro-1,1,2-tetrafluoropropene (244bb) is converted to 1234yf in the vapor phase in the presence of a catalyst.

According to any of the foregoing embodiments, also disclosed herein are compositions wherein the 2-chloro-1,1,2-tetrafluoropropene (244bb) is converted to 1234yf in the vapor phase in the absence of a catalyst.

According to any of the foregoing embodiments, also disclosed herein are compositions further comprising at least one oligomer.

According to any of the foregoing embodiments, wherein the oligomer has a structure of:

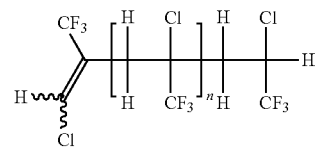

wherein n=0 to 9.

According to any of the foregoing embodiments, also disclosed herein are compositions further comprising at least one solvent. Examples of solvents comprise at least one of ketone, ether, amide, sulfone, chlorocarbons, chlorofluorocarbons, hydrochlorocarbons and hydrochlorofluorocarbons. And, in one particular embodiment, a solvent capable of dissolving 1233xf oligomers.

According to any of the foregoing embodiments, wherein the solvent comprises at least one member selected from the group consisting of 113a, dichloromethane, acetone, tetrahydrofuran (THF), $CHCl_3$, 1233xf, 244bb, $CCl_4$, 114a, 114, 113, 243db, 250fb, 1230xa, 240db, 1233zd, 1223xd, 1224yd, and 253fb.

In yet another embodiment, disclosed herein are 2,3,3,3-tetrafluoropropene (1234yf) compositions produced by the steps of: contacting a 1233xf containing composition in the vapor phase, with hydrogen fluoride in the presence of a fluorination catalyst at a temperature sufficient to effect formation of 2-chloro-1,1,1,2-tetrafluoropropene (244bb); and thermally dehydrochlorinating the 2-chloro-2,3,3,3-tetrafluoropropane (244bb) to 1234yf, or contacting the 2-chloro-2,3,3,3-tetrafluoropropane (244bb) with a vapor phase dehydrochlorination catalyst to effect dehydrochlorination to form 2,3,3,3-tetrafluoropropene (1234yf), or contacting the 2-chloro-2,3,3,3-tetrafluoropropane (244bb) with a base at a temperature sufficient to effect dehydrochlorination to form 2,3,3,3-tetrafluoropropene (1234yf).

The various embodiments can be used alone or in combinations with each other. Other features and advantages of the present invention will be apparent from the following more detailed description, taken in conjunction with the accompanying drawings which illustrate, by way of example, the principles of the invention.

DETAILED DESCRIPTION

The foregoing general description and the following detailed description are exemplary and explanatory only and are not restrictive of the invention.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

The transitional phrase "consisting of" excludes any element, step, or ingredient not specified. If in the claim such would close the claim to the inclusion of materials other than those recited except for impurities ordinarily associated therewith. When the phrase "consists of" appears in a clause of the body of a claim, rather than immediately following the preamble, it limits only the element set forth in that clause; other elements are not excluded from the claim as a whole.

The transitional phrase "consisting essentially of" is used to define a composition, method that includes materials, steps, features, components, or elements, in addition to those literally disclosed provided that these additional included materials, steps, features, components, or elements do materially affect the basic and novel characteristic(s) of the claimed invention, especially the mode of action to achieve the desired result of any of the processes of the present invention. The term 'consisting essentially of' occupies a middle ground between "comprising" and 'consisting of'.

Where applicants have defined an invention or a portion thereof with an open-ended term such as "comprising," it should be readily understood that (unless otherwise stated) the description should be interpreted to also include such an invention using the terms "consisting essentially of" or "consisting of".

Also, use of "a" or "an" are employed to describe elements and components described herein. This is done merely for convenience and to give a general sense of the scope of the invention. This description should be read to include one or at least one and the singular also includes the plural unless it is obvious that it is meant The term "selectivity," as used herein, means the ratio of the numbers of moles of the desired product to the number of moles of the desired product plus undesired products expressed as a percentage.

The term "yield," as used herein, means the ratio of the amount of product produced to the theoretical maximum amount of product, based on the amount of the limiting reagent.

Unless otherwise defined, all technical and scientific terms used herein have the same meaning as commonly understood by one of ordinary skill in the art to which this invention belongs. In case of conflict, the present specification, including definitions, will control. Although methods and materials similar or equivalent to those described herein can be used in the practice or testing of embodiments of the present invention, suitable methods and materials are described below. In addition, the materials, methods, and examples are illustrative only and not intended to be limiting.

Provided is a method of making hydrofluoro-olefins (HFOs) from hydrochloro-olefin hydrochlorofluoro-olefin, and hydrochlorofluorocarbon reagents and intermediates. In an exemplary embodiment, 2-chloro-3,3,3-trifluoropropene (1233xf) is produced via the dehydrochlorination of 2,3-dichloro-1,1,1-trifluoropropane (243db).

The processes of the invention may be conducted in a reactor suitable for a vapor phase reaction. The reactor is made of a material that is resistant to the reactants employed. The reactor may be constructed from materials which are resistant to the corrosive effects of hydrogen chloride and or hydrogen fluoride such as stainless steel, Hastelloy, Inconel, Monel, gold or gold-lined or quartz. The reactions may be conducted batch wise, continuous, semi-continuous or combinations thereof. Suitable reactors include batch reactor vessels and tubular reactors.

In a first embodiment, 2,3-dichloro-1,1,1-trifluoropropane (243db), in the vapor phase, undergoes a dehydrochlorination reaction to form 2-chloro-3,3,3-trifluoropropene (1233xf), as shown in Scheme (1).

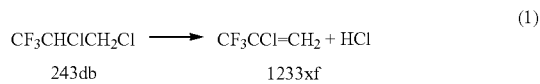

(1)

$$CF_3CHClCH_2Cl \longrightarrow CF_3CCl{=}CH_2 + HCl$$
243db                                 1233xf In one embodiment, the dehydrochlorination is a thermally driven process in the presence of a dehydrochlorination catalyst. Suitable catalysts include activated carbon, alumina, chromium oxide, oxides of transition metals, metal halides, and combinations thereof. When employing a vapor phase thermally driven process the contact time can range from about 10 seconds to about 5 minutes, about 30 seconds to about 4 minutes and in some cases, about 1 to about 3 minutes. Desirable results have been obtained by using activated carbon and metal halide on carbon catalysts and can achieve a selectivity to form 1233xf of about 90 to about 99%.

In another embodiment, when employing an alumina or chromium oxide catalyst for a vapor phase thermally driven dehydrochlorination process, the selectivity of the reaction versus the constitutional isomer 1-chloro-3,3,3-trifluoro-1-propene (1233zd) is typically observed over a range of about 50 to about 92 percent. If hydrogen fluoride (HF) is co-fed with the 243db into the reaction when alumina or chrome oxide catalyst is used, the formation of 1233zd is suppressed, resulting in improved selectivity of the 1233xf. The molar ratio of HF/243db can range from about 0.5 to about 5, about 1 to about 4.5 and, in some cases, about 2 to 4. In some embodiments, the selectivity of 1233xf formation may be at greater than about 80 percent, greater than about 92 percent, or greater than about 95 percent. Without wishing to be bound by any theory or explanation, selectivity in 1233xf formation can be increased by employing HF.

In a second embodiment, the dehydrochlorination may be performed in the liquid phase by contacting the 243db with a strong base, such as sodium hydroxide, potassium hydroxide, potassium tert-butoxide, calcium oxides, or calcium hydroxide. The molar ratio of base to 243db can range from about 0.1 to about 2, about 0.5 to about 1.75 and, in some cases, about 0.75 to about 1.5. Desirable results have been obtained from using a base comprising NaOH. The liquid phase dehydrochlorination may be performed in the presence or absence of a phase transfer catalyst. In some embodiments, the phase transfer catalyst may include a quaternary ammonium salt, a phosphonium salt, or a crown ether. The amount of phase transfer catalyst can range from about 0.1 to about 3% by weight, about 0.5 to about 2.5% and, in some cases, about 1 to about 2%. Desirable results can be obtained by using quaternary ammonium.

Another embodiment relates to a composition comprising at least one oligomer. The oligomer can comprise at least one of one or more 1233 monomers, 1233 dimers, 1233 trimers and higher molecular weight 1233 oligomers. The composition can be obtained when converting 243db into 1233xf, during storage of a 1233xf containing composition at an elevated temperature and exposure to an initiator. Examples of initiators comprise at least one of Lewis acids and oxidants (e.g., O2 and air). A further embodiment relates to a composition comprising 1233xf as well as at least one of the foregoing oligomers. In one aspect of this embodiment, the 1233xf oligomer has the following structure:

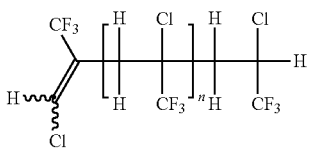

The oligomeric structure can vary including a non-linear backbone, branching groups and a double bond present inside as a terminal, internal or branch. "n" can range from 0 (dimer) to 9 and, typically, n corresponds to a trimer of 3 to 9 or 4 to 9.

In another embodiment of the invention the repeating unit of the oligomer can comprise a telomer:

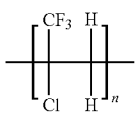

In a further embodiment, the 1233xf containing composition can comprise at least one additional compound selected from the group consisting of 1243zf, 244bb, 1224 isomer (e.g., 1224yd), 1230xa, 1231xf, 1233zd, 1233xfB (2-bromo-3,3,3-trifluoropropene), 1223xd, 1223za, 1232xf, 243db, 3,3,3-trifluoropropyne, 1-chloro-3,3,3-trifluoropropyne, 234bb, 233ab and 123. In a still further embodiment, the composition can comprise 1233xf, at least one 1233 oligomer and at least one additional compound. The amount of oligomer can range from greater than 0 to 2%, about 0.1% to 1.8% and, in some cases, about 0.2% to 1.5% of the composition. The amount of the additional compound can range from greater than 0 to about 5%, about 0.1% to about 4% and, in some cases, about 0.2% to about 3% of the composition. The compositions of these embodiments can also be prepared by blending various compounds in order to obtain the desired composition. The amount of oligomer can be increased by increasing temperature, exposure to oxidants (e.g., O2 and air) and contact with a Lewis acid.

In one embodiment, oligomer and 1233xf can be separated by distillation, adsorption, centrifuge and or filtration.

In another embodiment, if present, the oligomer can be dissolved by contacting a composition containing the oligomer with at least one solvent. In one particular embodiment, a precipitated or solid oligomer is dissolved and the solvated oligomer is removed. Examples of suitable solvents comprise at least one member selected from the group consisting of 113a, dichloromethane, acetone, THF, CHCl$_3$, 1233xf, 244bb, CCl$_4$, 114a, 114, 113, 243db, 250fb, 1230xa, 240db, 1233zd, 1223xd, 1224yd and 253fb. While any suitable amount of solvent can be employed, the ratio of solvent to oligomer can range from about 3:1 to 200:1, about 10:1 to about 175:1 and, in some cases, about 25:1 to about 150:1. In a further embodiment, solvent can be used to remove oligomer from a composition comprising 1233xf, oligomer and optionally at least one additional compound.

For a vapor phase dehydrochlorination process, the temperature in the reaction zone may be from about 325° C. to about 450° C. The preferred temperature will vary as a function of the catalyst described herein. The pressure employed for the vapor phase process can range from about atmospheric to about 100 psig. The dehydrochlorination process can be conducted at superatmospheric, atmospheric, or subatmospheric pressures. The contact time of the starting material with the catalyst can be largely varied. Typically, the contact time is from about 10 seconds to about 150 seconds. In some embodiments of this invention, the contact time is from about 20 seconds to about 80 seconds.

When a liquid phase process is employed, the temperature can range from about 20 to about 100° C., about 25 to 75° C. and, in some cases, about 30 to about 70° C. The liquid phase process time can range from about 10 minutes to 4 hours, about 30 minutes to about 3 hours and, in some cases, about 1 hour to about 2 hours.

The contacting step may be carried out by methods known in the art. In some embodiments of this invention, starting material, optionally with an inert gas, is fed to a reactor containing the catalyst. In some embodiments of this invention, starting material, optionally with an inert gas, is passed through the catalyst bed in a reactor. In some embodiments of this invention, starting material, optionally with an inert gas, may be mixed with the catalyst in a reactor with stir or agitation.

The dehydrochlorination process may be conducted in the presence of an inert gas such as He, Ar, or N$_2$. In some embodiments of this invention, the inert gas is co-fed into the reactor with the starting material. The amount of inert gas can range from about 5 to about 200%, about 10 to about 150% and, in some cases, about 25 to about 100% by volume of the organic starting materials.

In some embodiments, carbons are suitable as the dehydrochlorination catalyst. Carbon used in the embodiments of this invention may come from any of the following sources: wood, peat, coal, coconut shells, bones, lignite, petroleum-based residues and sugar. Commercially available carbons which may be used include those sold under the following trademarks: Barneby & Sutcliffe™, Darco™, Nucharm, Columbia JXN™, Columbia LCK™, Calgon™ PCB, Calgon™ BPL, Westvaco™, Norit™, Takeda™ and Barnaby Cheny NB™.

The carbon also includes three-dimensional matrix porous carbonaceous materials. Examples are those described in U.S. Pat. No. 4,978,649; hereby incorporated by reference. In one embodiment of the invention, carbon includes three-dimensional matrix carbonaceous materials which are obtained by introducing gaseous or vaporous carbon-containing compounds (e.g., hydrocarbons) into a mass of granules of a carbonaceous material (e.g., carbon black); decomposing the carbon-containing compounds to deposit carbon on the surface of the granules; and treating the resulting material with an activator gas comprising steam to provide a porous carbonaceous material. A carbon-carbon composite material is thus formed.

Embodiments of carbon catalysts include both non-acid washed, acid-washed, caustic washed carbons. In some embodiments, suitable carbon catalysts may be prepared by treating the carbon with acids such as HNO$_3$, HCl, HF, H$_2$SO$_4$, HClO$_4$, CH$_3$COOH, and combinations thereof. Acid treatment is typically sufficient to provide carbon that contains less than 1000 ppm of ash. Some suitable acid treatments of carbon are described in U.S. Pat. No. 5,136,113; hereby incorporated by reference. In some embodiments, an activated carbon is dried at an elevated temperature and then is soaked for 8 to 24 hours with occasional stirring in 1 to 12 weight percent of HNO$_3$. The soaking process can be conducted at temperatures ranging from room temperature to 80° C. The activated carbon is then filtered and washed with deionized water until the washings have a pH greater than 4.0 or until the pH of the washings does not change. Finally, the activated carbon is dried at an elevated temperature.

In some embodiments, the carbon is an activated carbon. In some embodiments, the carbon is a non-acid washed activated carbon. In some embodiments of this invention, the carbon is an acid washed activated carbon. The carbon can be in the form of powder, granules, or pellets, et al.

The 2-chloro-3,3,3-trifluoropropene (1233xf) may be purified before further use. In some embodiments, the 2-chloro-3,3,3-trifluoropropene (1233xf) is purified by distillation. In one embodiment, the distillation may be performed by heating the reaction mixture to a temperature less than the boiling point of 2,3-dichloro-1,1,1-trifluoropropane (243db) and greater than the boiling point of 2-chloro-3,3,3-trifluoropropene (1233xf), where the temperatures depend upon the pressure the reaction is conducted. The 1233xf recovered by heating the reaction mixture can be dried by methods known in the art including one or more of condensing and decanting the aqueous phase, passing the 1233xf phase through molecular sieves, and removing water from the 1233xf phase as the azeotrope. Unreacted 2,3-dichloro-1,1,1-trifluoropropane (243db) may be collected and recycled to the reaction to increase yield. The aqueous salt phase can be removed from the unreacted 243db phase by decantation.

In a third embodiment, 2-chloro-3,3,3-trifluoropropene (HCFC-1233xf) may be produced by vapor phase fluorination of a chlorocarbon or mixed chlorocarbon feed comprising one or more materials selected from the group of 1,1,1,2,3-pentachloropropane (HCC-240db), 2,3,3,3-tetrachloropropene (1230xf), and 1,1,2,3-tetrachloropropene (HCC-1230xa), with hydrogen fluoride to produce a product stream comprising hydrogen fluoride, 2-chloro-3,3,3-trifluoropropene (1233xf) and hydrogen chloride. The yield of 1233xf in the product stream can range from about 80% to about 99.9%, about 85% to about 99% and, in some cases, about 88% to about 99%.

The reaction of the third embodiment may be conducted as a vapor phase process. The reactor is filled with a vapor phase fluorination catalyst. Any fluorination catalysts known in the art may be used in this process. Suitable catalysts include, but are not limited to chromium, aluminum, cobalt, manganese, nickel and iron oxides, hydroxides, halides, oxyhalides, inorganic salts thereof and their mixtures. Combinations of catalysts suitable for the present invention nonexclusively include $Cr_2O_3$, $FeCl_3/C$, $Cr_2O_3/Al_2O_3$, $Cr_2O_3/AlF_3$, $Cr_2O_3$/carbon, $CoCl_2/Cr_2O_3/Al_2O_3$, $NiCl_2/Cr_2O_3/Al_2O_3$, $CoCl_2/AlF_3$, $NiCl_2/AlF_3$ and mixtures thereof. Chromium oxide/aluminum oxide catalysts are described in U.S. Pat. No. 5,155,082 which is incorporated herein by reference. Chromium (III) oxides such as crystalline chromium oxide or amorphous chromium oxide are preferred with amorphous chromium oxide being most preferred. Chromium oxide ($Cr_2O_3$) is a commercially available material which may be purchased in a variety of particle sizes. Fluorination catalysts having a purity of at least 98% are preferred. The fluorination catalyst is present in an excess but in at least an amount sufficient to drive the reaction.

The reactor is preheated to the fluorination reaction temperature while anhydrous HF is fed to the reactor. The stream containing the chlorocarbon feed material, for example the 1,1,2,3-tetrachloropropene, and optionally a stabilizer is introduced into the reaction vessel next, which is maintained at the desired temperature. While any suitable stabilizer can be employed, an example of a stabilizer, comprises triethyl amine. The amount of stabilizer can be greater than 0 to about 100 ppm, about 10 ppm to 90 ppm and, in some cases, about 25 ppm to about 50 ppm. The 1,1,2,3-tetrachloropropene (HCC-1230xa) and HF may be fed to the reactor at any convenient temperature and pressure. In a preferred embodiment either or both of the HCC-1230xa and the HF are pre-vaporized or preheated to a temperature of from about 30° C. to about 300° C. prior to entering the reactor. In another embodiment, the HCC-1230xa and HF are vaporized in the reactor. The HF and HCC-1230xa feeds are then adjusted to the desired mole ratio. The HF to HCC-1230xa mole ratio preferably ranges from about 3:1 to about 100:1; more preferably from about 4:1 to about 50:1 and most preferably from about 5:1 to about 20:1.

The vapor phase fluorination reaction is conducted at a preferred temperature ranging from about 80° C. to about 400° C.; more preferably from about 100° C. to about 350° C. and most preferably from about 200° C. to about 330° C. Reactor pressure is not critical and can be super-atmospheric, atmospheric or under vacuum. The vacuum pressure can be from about 5 torr (0.0966 psig) to about 760 torr (14.69 psig). During the vapor phase fluorination reaction, HCC-1230xa and HF are reacted in a vapor phase in the presence of the fluorination catalyst. The reactant vapor is allowed to contact the fluorination catalyst for from about 1 to 120 seconds or more preferably from about 1 to 20 seconds.

The reactions described above may result in the formation of additional reaction products. In some embodiments, the reaction additional reaction products include at least one compound selected from the group consisting of 1,2-dichloro-3,3,3-trifluoropropene (1223xd), 2,3-dichloro-3,3-difluoropropene (1232xf), 2,2,3-trichloro-1,1,1-trifluoro-propane (233ab), 2,3,3-trichloro-1,1,1-trifluoro-propane (233da), 3,3,3-trifluoropropyne, 1-chloro-3,3,3-trifluoropropyne, 3,3,3-trifluoro propene (1243zf), 1-chloro-3,3,3-trifluoro-1-propene (1233zd), 1-chloro-2,3,3,3-tetrafluoro-1-propene (1224yd), and 2-bromo-3,3,3-trifluoropropene. Compositions including 1233xf and at least one member selected from the group consisting of 1,2-dichloro-3,3,3-trifluoropropene (1223xd), 2,3-dichloro-3,3-difluoropropene (1232xf), 2,2,3-trichloro-1,1,1-trifluoro-propane (233ab), 2,3,3-trichloro-1,1,1-trifluoro-propane (233da), 3,3,3-trifluoropropyne, 1-chloro-3,3,3-trifluoropropyne, 3,3,3-trifluoro-1-propene (1243zf), 1-chloro-3,3,3-trifluoro-1-propene (1233zd), 1-chloro-2,3,3,3-tetrafluoro-1-propene (1224yd), and 2-bromo-3,3,3-trifluoropropene, can be prepared by blending 1233xf with at least one of the foregoing members. In one embodiment of the invention, the member comprises at least one of 1-chloro-3,3,3-trifluoropropyne, 2-bromo-3,3,3-trifluoropropene, 1-chloro-3,3,3-trifluoro-1-propene (1233zd), 1,2-dichloro-3,3,3-trifluoropropene (1223xd), or 1-chloro-2,3,3,3-tetrafluoro-1-propene (1224yd). The amount of the member in the composition can range from greater than 0 weight percent to about 10 weight percent, about 0.01 weight percent to about 5 weight percent, about 0.1 weight percent to about 2 weight percent and, in some cases about 0.1 wt % to about 100ppmw.

Compositions including 2-chloro-3,3,3-trifluoropropene (1233xf) may be used in various applications as a heat transfer material having a low global warming potential. Suitable applications include, but are not limited to, heat pipes, refrigeration systems, immersion cooling systems, and as a cleaning solvent. 2-chloro-3,3,3-trifluoropropene (1233xf) can additionally be used as a reactive intermediate for the production of further hydrofluorocarbon compounds, many of which also exhibit low global warming potentials.

Compositions including 2-chloro-3,3,3-trifluoropropene (1233xf) may also be used as intermediates to form additional fluorinated compounds. In an embodiment, 2-chloro-3,3,3-trifluoropropene (1233xf), in the liquid phase, is contacted with hydrogen fluoride, in the presence of a catalyst, and undergoes a hydrofluorination reaction to form 2-chloro-1,1,1,2-tetrafluoropropane (244bb), as shown in Scheme (2).

(2)

In one embodiment, the catalyst is a Lewis acid catalyst such as $SbCl_5$, $TiCl_4$, $SbF_5$, $SnCl_4$, $SbCl_3$, $TaF_4$, or $TiF_4$. In one embodiment, the Lewis acid catalyst is an antimony-based compound represented by $SbCl_xF_{5-x}$. The selectivity of the reaction is typically in the range of 80 to 99 percent, or 90 to 99 percent. The yield of the reaction is typically at least 90 percent. In some embodiments, the yield is greater than 95 percent, greater than 97 percent, or greater than 99 percent. Examples of suitable reaction conditions are described in WO 2007/079431; the disclosure of which is hereby incorporated by reference.

Alternatively, the hydrofluorination may be performed in the vapor phase in the presence of a catalyst. Suitable vapor phase catalysts include antimony chloride on carbon ($SbCl_5$/C). The selectivity of the vapor phase process may be greater than 95 percent, greater than 97 percent, or greater than 98 percent. Yields have been observed up to about 92 percent. Examples of suitable reaction conditions are described in US 20090182179 A1; the disclosure of which is hereby incorporated by reference In an embodiment, 1-chloro-1,1,1,2-tetrafluoropropene (244bb), in the vapor phase, undergoes a dehydrochlorination reaction to form 2,3,3,3-tetrafluoropropene (1234yf), as shown in Scheme (3).

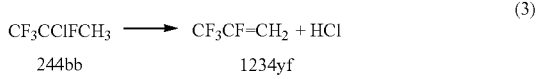
(3)

The reaction proceeds by thermally dehydrochlorinating the 2-chloro-2,3,3,3-tetrafluoropropane (244bb) to 1234yf, or contacting the 2-chloro-2,3,3,3-tetrafluoropropane (244bb) with a vapor phase dehydrochlorination catalyst to effect dehydrochlorination to form 2,3,3,3-tetrafluoropropene (1234yf), or contacting the 2-chloro-2,3,3,3-tetrafluoropropane (244bb) with a base at a temperature sufficient to effect dehydrochlorination to form 2,3,3,3-tetrafluoropropene (1234yf). Examples of suitable process conditions are disclosed by US20110270000, CN103483142, and WO 2019203318; the disclosure of which are hereby incorporated by reference.

In one embodiment, the dehydrochlorination is a thermally driven and vapor phase process in the presence of a dehydrochlorination catalyst. Suitable catalysts include activated carbon, Pd/C, Pt/C, $MgF_2$, $Cr_2O_3$, MgO, $FeCl_3$, CsCl/$MgF_2$, and KCl/C. The selectivity of the reaction may be between 80 and 92 percent, or between 85 and 90 percent. The catalyst contact time can range from about 10 seconds to about 5 minutes, about 30 seconds to about 4 minutes and, in some cases, about 1 to about 3 minutes.

In one embodiment, the dehydrochlorination may be conducted without a catalyst by a thermal pyrolysis route. In one embodiment, the reaction mixture is heated to about 400 to 500° C. in the absence of oxygen. By "absence of oxygen" it is meant that less than about 100 ppmv of oxygen is present during the dehydrochlorination. Selectivity of greater than 98 percent may be achieved.

Alternatively, the dehydrochlorination may be performed in the liquid phase by contacting the 244bb with a strong base, such as sodium hydroxide, potassium hydroxide, potassium tert-butoxide, calcium oxides, or calcium hydroxide, in the presence of a catalyst. Suitable catalysts include transition metals with activated carbon, such as Pt/C. The selectivity of liquid phase dehydrochlorination may be about 92 to 96 percent. In some embodiments, the reaction may be performed at a temperature of 70 to 130° C. Examples of suitable reaction conditions and reactant ratios can be found in US20110270000, CN103483142, and WO 2019203318; the disclosures of which are hereby incorporated by reference.

In an embodiment, 2-chloro-3,3,3-trifluoropropene (1233xf), in the vapor phase, is contacted with hydrogen fluoride, in the presence of a catalyst, and undergoes conversion to form 2,3,3,3-tetrafluoropropene (1234yf), as shown in Scheme (4).

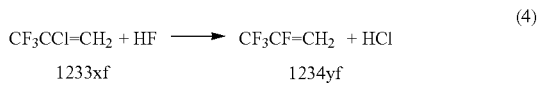
(4)

In one embodiment, the catalyst is a halogenated metal catalyst such as fluorinated chromium oxide, fluorinated $Al_2O_3$, fluorinated chromium oxide supported on carbon, fluorinated $Al_2O_3$ supported on carbon, chromium halide. The selectivity of the reaction is typically in the range of 20 to 90 percent, about 30 to about 85% or, in some cases, about 65 to about 90 percent. The yield of the reaction is typically at least 90 percent. In some embodiments, the yield is greater than 95 percent, greater than 97 percent, or greater than 99 percent. Examples of suitable reaction conditions and ratio of reactants are disclosed in US 20120078020A1; the disclosure of which is hereby incorporated by reference.

The 2,3,3,3-tetrafluoropropene (1234yf) may be further purified. In some embodiments, the 2,3,3,3-tetrafluoropropene (1234yf) is purified by distillation. In one embodiment, the distillation may be performed by cooling the reaction mixture to a temperature less than the boiling point of 2,3,3,3-tetrafluoropropene (1234yf) (−29.5° C.). Unreacted 1-chloro-1,1,1,2-tetrafluoropropene (244bb) may be recycled to the reaction to increase yield. When 1233xf is vaporized before it is fed into reactor to make 244bb, oligomer can be left in vaporizer and causes fouling of vaporizer, the solvent can be used to dissolve oligomer and remove the deposed oligomer from vaporizer. 1233xf oligomer could also accumulate at the bottom of distillation column when 1233xf is distilled, the solvent can be used to dissolve oligomer and remove the deposed oligomer from distillation packing. To remove solid polymer from a vessel such as, but not limited to, a heat exchanger or distillation column, the process fluid comprising 1233xf is removed and a solvent is added. The solvent can either be held in the vessel or it can be circulated through the vessel. Heat can be applied to increase the temperature to aid dissolution of the polymer. After sufficient time to dissolve the 1233xf polymer, which as an example can be between 2 and 12 hours, the solvent is removed and the process fluid comprising 1233xf is re-introduced, The following Examples are provided to illustrate certain embodiments of the invention and shall not limit the scope of the appended claims.

EXAMPLES

Example 1: 243db Dehydrochlorination to 1233xf by 30% NaOH at 35° C.

100 g 243db, 20 g 30 wt % NaOH and 0.25 g TBAB were charged into a 400 ml autoclave reactor. The reactor was sealed and then heated up to 35° C. with agitation. The reactor was agitated at 35° C. for 1 hour, then 20 g of 30 wt % NaOH was added into reactor every hour for 3 times. After all the NaOH solution is added, it was stirred at 35° C. for another 3 hours. The reactor was cooled down to room temp. An organic liquid sample was drawn from a dip tube and analyzed by GC-MS-FID using a GasPro RTx 1 column. The GC analysis of product are listed in Table 1 below.

TABLE 1

| Compounds | | GC area % |
|---|---|---|
| 1243zf | $CF_3CH=CH_2$ | 0.0001% |
| CH3Cl | $CH_3Cl$ | 0.0002% |
| CF3C::CCl | $CF_3=CCl$ | 0.0002% |
| 1224yd | Z—$CF_3CF=CHCl$ | 0.0001% |
| 1233xf | $CF_3CCl=CH_2$ | 94.6092% |
| 1233zd | $CF_3CH=CHCl$ | 0.0002% |
| CF3C::CF | $CF_3C=CF$ | 0.0006% |
| 1224yd | E-$CF_3CF=CHCl$ | 0.0072% |
| 123 | $CF_3CHCl_2$ | 0.0008% |
| 1233xfB | $CF_3CBr=CH_2$ | 0.0035% |
| 1223xd | Z—$CF_3CCl=CHCl$ | 0.1005% |
| 1223za | $CF_3CH=CCl_2$ | 0.0001% |
| 1232xf | $CClF_2CCl=CH_2$ | 0.0249% |
| 1223xd | E—$CF_3CCl=CHCl$ | 0.0073% |
| 243db | $CF_3CHClCH_2Cl$ | 5.1619% |
| 1232 | $C3H2ClF2$ | 0.0013% |
| CF3CHClCH2OH | | 0.0025% |
| 233ab | $CF_3CCl_2CH_2Cl$ | 0.0323% |
| 1231xf | $CCl_2FCCl=CH_2$ | 0.0075% |
| (CF3CHClCH2)2O | | 0.0038% |
| 1230xa | $CH2ClCCl=CCl2$ | 0.0021% |
| Unknown others | | 0.0337% |

Example 2: 243db Dehydrochlorination to 1233xf by 30% NaOH at 45° C.

100 g 243db, 92 g 30 wt % NaOH and 0.5 g TBAB were charged into a 400 ml autoclave reactor. The reactor was sealed and then heated up to 45° C. with agitation. The reactor was agitator at 45° C. for 2 hours and was cooled down to −10° C. The reactor was opened and liquid phase of organic was analyzed by GC-MS-FID using a GasPro RTx 1 column. The GC analysis of product are listed in Table 2 below.

TABLE 2

| Compounds | | GC area % |
|---|---|---|
| Trifluoropropyne | $CF_3C=CH$ | 0.0084% |
| CH3Cl | $CH_3Cl$ | 0.0003% |
| CF3C:CCl | $CF_3=CCl$ | 0.0492% |
| 1233xf | $CF_3CCl=CH_2$ | 99.8420% |
| 1233zd | $CF_3CH=CHCl$ | 0.0004% |
| CF3C::CF | $CF_3C=CF$ | 0.0005% |
| 1224yd | $CF_3CF=CHCl$ | 0.0012% |
| 123 | $CF_3CHCl_2$ | 0.0009% |
| 1233xfB | $CF_3CBr=CH_2$ | 0.0032% |

TABLE 2-continued

| Compounds | | GC area % |
|---|---|---|
| 1223xd | Z—$CF_3CCl=CHCl$ | 0.0321% |
| 1223za | $CF_3CH=CCl_2$ | 0.0028% |
| C6H3F9 | | 0.0013% |
| 1232xf | $CClF_2CCl=CH_2$ | 0.0218% |
| 1223xd | E—$CF_3CCl=CHCl$ | 0.0102% |
| 243db | $CF_3CHClCH_2Cl$ | 0.0019% |
| 233ab | $CF_3CCl_2CH_2Cl$ | 0.0024% |
| 1231xf | $CCL_2FCCl=CH_2$ | 0.0056% |
| C6H5ClF6 | | 0.0070% |
| (CF3CCHClCH2)2O | | 0.0033% |
| Unknown others | | 0.0054% |

Example 3: 243db Dehydrochlorination to 1233xf by 30% NaOH at 5° C.

100 g 243db, 23 g 30 wt % NaOH, 4 g water and 0.2 g TBAB were charged into a 400 ml autoclave reactor. The reactor was sealed and then heated up to 55° C. with agitation. The reactor was agitated at 55° C. for 1 hours, then 20 g of 30 wt % NaOH was added into the reactor every hour for 3 times. After all the NaOH solution is added, it was stirred at 55° C. for another 4 hours. Reactor was cooled down to room temp. An organic liquid sample was draw from a dip tube and analyzed by GC-MS-FID using a GasPro RTx 1 column. The GC analysis of product are listed in Table 3 below.

TABLE 3

| | Compound | GC area % |
|---|---|---|
| 1234yf | $CF_3CF=CH_2$ | 0.0117% |
| 1243zf | $CF_3CH=CH_2$ | 0.0001% |
| 40 | $CH_3Cl$ | 0.0004% |
| CF3C::CCl | $CF_3C=CCl$ | 0.0002% |
| 1233xf | $CF_3CCl=CH_2$ | 97.1296% |
| 1233zd | $CF_3CH=CHCl$ | 0.0004% |
| CF3C::CF | $CF_3C=CF$ | 0.0007% |
| 1224yd | Z—$CF_3C_F=CHCl$ | 0.0021% |
| 123 | $CF_3CHCl_2$ | 0.0008% |
| 1233xfB | $CF_3CBr=CH_2$ | 0.0033% |
| 1223xd | Z—$CF_3CCl=CHCl$ | 0.0852% |
| 1232xf | $CClF_2CCl=CH_2$ | 0.0203% |
| 1223xd | E—$CF_3CCl=CHCl$ | 0.0058% |
| 243db | $CF_3CHClCH_2Cl$ | 2.6909% |
| 1232 | $C3H2Cl2F2$ | 0.0011% |
| CF3CHClCH2OH | | 0.0029% |
| 233ab | $CF_3CCl_2CH_2Cl$ | 0.0213% |
| 1231 | $CCl_2FCCl=CH_2$ | 0.0051% |
| (CF3CHClCH2)2O | | 0.0022% |
| Unknown others | | 0.0160% |

Example 4 Oligomer Analysis Using GC/MS 100 g 243db, 23 g 30 wt % NaOH, 4 g water and 0.2 g TBAB were charged into a 400 ml autoclave reactor. The reactor was sealed and then cooled to 0° C. with agitation. The reactor was agitated at 0° C. for 1 hours, then 20 g of 30 wt % NaOH was added into the reactor every hour for 3 times. After all the NaOH solution is added, the contents of the reactor was stirred at 0° C. for another 4 hours. Reactor was allowed to reach room temp. An organic liquid sample was drawn from a dip tube and analyzed by GC-MS-FID using a GasPro RTx 1 column. The GC analysis of product are listed in Table 4 below.

TABLE 4

| Compounds | GC area % |
| --- | --- |
| CF3C::CCl | 0.0061% |
| 244bb | 0.0053% |
| 1233xf | 99.9726% |
| 1233zd | 0.0037% |
| 1224yd | 0.0032% |
| 233ab | 0.0011% |
| CF3CBr=CH2 | 0.0025% |
| 1233-dimer n = 0 | 0.0002% |
| C6HCl2F7 | 0.0006% |
| 250fb | 0.0004% |
| 1233-trimer n = 1 | 0.0004% |
| 1233-trimer n = 2 | 0.0014% |
| 1233-trimer n = 3 | 0.0001% |
| Others | 0.0023% |

Example 5: Oligomer Analysis Using GC/MS—Liquid Chromatography (LC)

Into a 400 ml Hastelloy lined shaker tube was added 100 grams of 1233xf and 23 grams of HF. The tube was heated while shaking to 130 C for 24 hours. After 24 hours, the tube was allowed to cool to room temperature and aqueous potassium hydroxide solution (67.3 grams of solid KOH dissolved into 200 ml of water) was added. The test was repeated at 90 C and a portion of the organic layer from each test was removed and analyzed individually by GC/MS-FID (RTX column). Results of GC/MS are shown as area % in Table 5. Due to the detection limitations of the above GCMS system, only lower molecular weight oligomeric compounds are shown in Table 5.

TABLE 5

| | GC/MS results | |
| --- | --- | --- |
| Compound | 130 C. | 90 C. |
| n = 1 1233xf | 99.33% | 99.99% |
| n = 2 | 0.0020% | Not detected |
| n = 3 | 0.1390% | 0.0010% |
| n = 3, isomer 1 | 0.4680% | 0.0030% |
| n = 3, isomer 2 | 0.0570% | Not detected |
| Others, non telomeric material | 0.0040% | 0.0060% |

Higher molecular weight telomer oligomeric compounds were identified by using LCMS (Agilent 1290 Infinity II with 6520 QTOF, Column: Agilent InfinityLab Poroshell 120 EC-C18 (2.1×50 mm, 2.7 μm)). Results are shown in Table 6 as relative area percent with n=7 set to 100%. The GC/MS/LC analysis detected telomers having the following repeating unit.

1233xf telomer

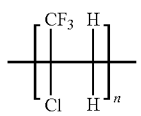

TABLE 6

| | LCMS result | | |
| --- | --- | --- | --- |
| n | m/z | 130 C. | 90 C. |
| 4 | | Not included in scan | |
| 5 | 651 | 59.34% | 40.09% |
| 6 | 781 | 85.42% | 72.06% |
| 7 | 911 | 100.00% | 100.00% |
| 8 | 1043 | 42.57% | 48.43% |
| 9 | 1173 | 25.08% | 31.68% |
| 10 | 1366 | 8.59% | 14.25% |
| 11 | 1496 | 0.35% | 0.80% |

While the invention has been described with reference to one or more embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims. In addition, all numerical values identified in the detailed description shall be interpreted as though the precise and approximate values are both expressly identified.

What is claimed is:

1. A composition comprising:
   a) 2-chloro-3,3,3-trifluoropropene (1233xf) in an amount at least 94% GC area, 1,2-dichloro-3,3,3-trifluoropropene (1223xd), 2,3-dichloro-3,3-difluoropropene (1232xf); and
   b) at least one additional compound selected from the group consisting of 2,3-dichloro-1, 1, 1-trifluoropropane (243db), 2,2,3-trichloro-1,1,1-trifluoro-propane (233ab), 2,3,3-trichloro-1,1,1-trifluoro-propane (233da), 3,3,3-trifluoropropyne, 1-chloro-3,3,3-trifluoropropyne, 3,3,3-trifluoro-1-propene (1243zf), 1-chloro-3,3,3-trifluoro-1-propene (1233zd), 1-chloro-2,3,3,3-tetrafluoro-1-propene (1224yd), 2-bromo-3,3, 3-trifluoropropene, and combinations thereof.

2. The composition of claim 1, wherein b) includes 2,3-dichloro-1,1,1-trifluoropropane (243db).

3. The composition of claim 1, wherein b) includes 1-chloro-3,3,3-trifluoropropyne.

4. The composition of claim 1, wherein b) includes 2-bromo-3,3,3-trifluoropropene (1233xfB).

5. The composition of claim 1, wherein the 1233xf is present in an amount of at least about 97% GC area.

6. A 2-chloro-3,3,3-trifluoropropene (1233xf) composition comprising 94% GC area 1233xf, 1,2-dichloro-3,3,3-trifluropropene (1223xd), 2,2,3-trichloro-1,1,1-trifluoropropane (233ab), and 2,3-dichloro3,3-difluoropropene (1232xf), and produced by the steps of:
   contacting 2,3-dichloro-1,1,1-trifluoropropane (243 db), in the liquid phase, with a base at a temperature between about 25° C. to about 75° C. to effect dehydrochlorination to form the 2-chloro-3,3,3-trifluoropropene (1233xf), 2,2,3-tricholoro- 1,1,1-trifluoropropane (233ab), 1,2-dichioro-3,3,3-trifluoropropene (1223xd) and 2,3-dichioro-3,3-difluoropropene (1232xf).

7. The composition of claim 6, wherein the base includes at least one of sodium carbonate, potassium carbonate, sodium hydroxide, potassium hydroxide, potassium tert-butoxide, calcium oxides, or calcium hydroxide.

8. The composition of claim 6, wherein the composition additionally includes at least one of 1-chloro-3,3,3-trifluoro-1-propene (1233zd), 2,3-dichloro-1,1,1-trifluoropropane (243 db), 2,3,3-trichloro-1,1,1-trifluoro-propane (233da), 3,3,3-trifluoropropyne, 1-chloro-3,3,3-trifluoropropyne, or 2-bromo-3,3,3-trifluoropropene (1233xfB).

9. A 2-chloro-3,3,3-trifluoropropene (HCFO-1233xf) composition including HCFO-1233xf in excess of 94% GC are and HCFC-233ab produced by the steps of:
contacting 2,3-dichloro-1,1,1-trifluoropropane (243db), in the vapor phase, with a dehydrochlorination catalyst at a temperature between about 325° C. to about 450° C. and pressure sufficient to effect dehydrochlorination to form the 2-chloro-3,3,3-trifluoropropene (1233xf) and HCFC-233ab.

10. The composition of claim 9, wherein the dehydrochlorination catalyst comprises activated carbon, alumina, chromium oxide, oxides of transition metals, or metal halides.

11. The composition of claim 9, wherein the composition further includes at least one of 2,3-dichloro-1,1,1-trifluoropropane (243db), 1,2-dichloro-3,3,3-trifluoropropene (1223xd), 2,3-dichloro-3,3-difluoropropene (1232xf), 2,3,3-trichloro-1,1,1-trifluoro-propane (233da), 3,3,3-trifluoropropyne, 1-chloro-3,3,3-trifluoropropyne, or 2-bromo-3,3,3-trifluoropropene (1233xfB).

12. The composition of claim 9 wherein the composition includes at least 95% GC area 1233xf and at least one additional compound selected from the group consisting of 1243zf, 244bb, 1224 isomer 1230xa, 1231xf, 1233zd, 1223xd, 1223za, 1232xf, 243db 3,3,3-trifluoropropyne, 1-chloro-3,3,3-trifluoropropyne, 234bb, 2-bromo-3,3,3-trifluoropropene (1233xfB) and 123.

13. The composition of claim 12 wherein the amount of the at least one additional compound is greater than 0 and less than 1wt. %.

14. A 2-chloro-3,3,3-trifluoropropene (1233xf) composition produced by the steps of:
contacting a compound selected from the group consisting of 1,1,1,2,3-pentachloropropane (HCC-240db), 2,3,3,3-tetrachloropropene (1230xf), 1,1,2,3-tetrachloropropene (HCC-1230xa), 2,3-dichloro-1,1,1-trifluoropropane (243db) and combinations thereof, in the vapor phase, with a carbon supported fluorination catalyst in the presence of hydrogen fluoride at a temperature and pressure sufficient to effect formation of 2-chloro-3,3,3-trifluoropropene (1233xf).

15. The composition of claim 14, wherein the fluorination catalyst comprises chromium, aluminum, cobalt, manganese, nickel or iron oxides, hydroxides, metal halides, oxyhalides, or inorganic salts thereof.

16. The composition of claim 1 further comprising at least one oligomer.

17. The composition of claim 13 further comprising at least one oligomer.

18. The composition of claim 16 wherein the oligomer has a structure of:

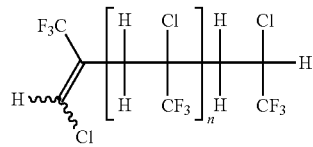

wherein n=0 to 9.

19. The composition of claim 17 wherein the oligomer has a structure of:

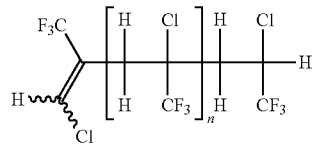

wherein n=0 to 9.

20. The composition of claim 16 further comprising at least one solvent capable of at least partially dissolving the oligomer.

21. The composition of claim 17 further comprising at least one solvent capable of at least partially dissolving the oligomer.

22. The composition of claim 20 wherein the solvent comprises at least one member selected from the group consisting of 113a, dichloromethane, acetone, THF, CHCl3, 1233xf, 244bb, CCl4, 114a, 114, 113, 243 db, 250fb, 1230xa, 240 db, 1233zd, 1223xd, 1224 yd, and 253fb.

23. The composition of claim 21 wherein the solvent comprises at least one member selected from the group consisting of 113a, dichloromethane, acetone, THF, CHCl3, 1233xf, 244bb, CCl4, 114a, 114, 113, 243 db, 250fb, 1230xa, 240 db, 1233zd, 1223xd, 1224 yd, and 253fb.

* * * * *